United States Patent
Pascaloff

[19]

[11] Patent Number: 6,113,619
[45] Date of Patent: Sep. 5, 2000

[54] TWO STAGE RELEASING INTERLOCKING SYSTEM

[75] Inventor: John H. Pascaloff, Keswick, Va.

[73] Assignee: Microaire Surgical Instruments, Charlottesville, Va.

[21] Appl. No.: 09/166,104

[22] Filed: Oct. 5, 1998

[51] Int. Cl.[7] .................................................. A61B 17/14
[52] U.S. Cl. ............................................ 606/178; 30/339
[58] Field of Search ............................ 606/176, 82, 178; 30/339

[56] References Cited

U.S. PATENT DOCUMENTS

| | | | |
|---|---|---|---|
| 494,070 | 3/1893 | Moffat et al. | 30/339 |
| 5,237,884 | 8/1993 | Seto | 606/178 |
| 5,265,343 | 11/1993 | Pascaloff | 30/339 |
| 5,383,785 | 1/1995 | Brugger | 433/129 |
| 5,458,346 | 10/1995 | Briggs | 30/339 |
| 5,729,904 | 3/1998 | Trott | 30/339 |
| 5,839,196 | 11/1998 | Trott | 30/339 |

*Primary Examiner*—Michael Buiz
*Assistant Examiner*—Jackie Tan-Uyent Ho
*Attorney, Agent, or Firm*—Whitham, Curtis & Whitham

[57] ABSTRACT

A two stage releasing interlocking system for mounting a medical device tool which includes a jaw head having an aperture. A collet having an upper portion and a lower portion is rotatably mounted within the jaw head. The upper portion of the collet has an aperture and is substantially aligned with the aperture of the jaw head. A moving means moves the lower portion of the collet into an opened position and a closed position with respect to the upper portion of the collet. Actuating means prevents the moving means from moving the lower portion of the collet into the opened position when the actuating means is in a first position and permits the moving means to move the lower portion of the collet into the opened position when the actuating means is in a second position.

18 Claims, 4 Drawing Sheets

TWO STAGE RELEASING INTERLOCKING SYSTEM

FIELD OF THE INVENTION

The present invention generally relates to an interlocking system and, more particularly, to a two stage releasing interlocking system used with, for example, sagittal saw blades.

BACKGROUND DESCRIPTION

There are countless medical devices that are currently being used by medical professionals, such as surgeons, dentists, etc. These medical devices include, amongst others, saws, drills, screw divers and other tools (collectively referred to as "tools").

In order to use these medical devices it is necessary to place the tool into a collet or chuck (collectively referred to as "collet"). Many of these collets, however, are designed so that a key is needed to open and close the collets so that the tool can be securely inserted therein. This poses several problems, one of which is that the keys and/or threads on the collet may become stripped in which case it is impossible for the user to open and close the collet, and the medical instrument must then be repaired or discarded. This also poses a safety concern because the key and/or threads on the collet may become stripped during an operation or other procedure, making it impossible for the medical professional to exchange tools during use thereof.

The medical professional may also lose the key which will render the medical device inoperable. Also, using a key during an operation or other procedure may be difficult because the user (e.g., surgeon or other medical professional) may not be able to properly grip the key in order to open and close the collet, or may drop the key in which case it is not sterile and can no longer be used during the instant procedure.

Spring loaded chucking systems used in medical devices are also well known in the medical field. However, these spring loaded systems are not robust, and in many instances the tool becomes loose and/or dislodged. In extreme cases, the tool may even become accidently released from the collet itself, making it very dangerous for both the medical professional and the patient. These spring loaded systems are also designed in such a manner that the medical professional may accidently "hit" the spring loaded release mechanism during use thereof. In this case, the tool can spontaneously eject from the medical device posing serious injuries to both the medical professional and the patient.

What is needed is a locking system that is easy to use and provides safeguards for both the medical professional using the medical device and the patient. Such a system would be keyless and would have safety features so that the tool cannot be accidently released from the medical device. This locking mechanism would be easy to manufacture and would further afford a stable platform for the tool.

SUMMARY OF THE INVENTION

The present invention is directed to a two stage releasing interlocking system. In a preferred embodiment, the two stage releasing interlocking system is used in medical devices, such as sagittal saw devices, where a hub of the tool (e.g., saw blade) locks into a collet of the medical device. Sagittal saw blades, for example, are easily installed and removed from the collet of the medical device using the interlocking system without the use of a wrench or other specialized tool (e.g., key). Also, the interlocking system prevents the collet from opening during use thereof, thus preventing the saw blade from being accidently released during the use of the medical device.

The interlocking system of the present invention includes, in part, a release rod positioned within a release button, both being positioned within a jaw head. The release button can only be depressed after the release rod is depressed, thus providing an additional safety feature so that the saw blade (or other tool) cannot be accidently removed from the collet of the medical device. The locking system of the present invention also provides a stable and robust platform for the saw blade (or other tool) within the medical device during use thereof.

The release button extends through an aperture of the jaw head and a yoke in order to communicate with a locking dish. The yoke and locking dish are collectively known as a collet. When the release button is depressed, the locking dish is lowered and the tool, such as the saw blade, may be inserted (or removed) from the collet. Once the saw blade or other tool is inserted between the yoke and the locking dish, a spring communicating with the release button urges the release button into a fully extended position (e.g., original upright position) thus locking the lock dish against the tool (e.g., the hub of the saw blade). The locking dish cannot be moved unless both the release rod and release button are fully depressed. This ensures that the hub of the saw blade remains fixed within the collet of the medical devices during use thereof.

In preferred embodiments, the release button, release rod, yoke and locking dish are freely rotatable with respect to the jaw head. In further preferred embodiments, the yoke includes downward projections which extend through apertures of the hub of the saw blade (or other tool) in order to fix the saw blade (or other tool) to the collet when the locking dish is in the closed position (and the release button is in the upright position).

A bearing system stabilizes the release button within the jaw head, and a spring system provides a means to force the release rod into a fully extended position (e.g., upright). A locking ball bearing system partially provides the mechanism for preventing the release button from being depressed prior to the release rod being depressed.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The present invention is directed to a two stage releasing interlocking system for use in medical devices. In a preferred embodiment, the two stage releasing interlocking system is used in medical devices, such as sagittal saw systems, where a hub of the saw blade locks into a collet of the two stage releasing interlocking system; however, other systems, such as, for example, drill bits, screw drivers and other tools, are equally contemplated for use with the present invention. Thus, the present invention is not limited to the use with sagittal saw blades, but is equally applicable to the use with other medical and non-medical tools. However, for illustrative purposes only, the use of saw blades and similar devices thereof will be discussed herein.

By using the two stage releasing interlocking system of the present invention, sagittal saw blades, for example, are easily installed and removed from the collet of the two stage releasing interlocking system without the use of a wrench or other specialized tool (e.g., key). Also, the two stage releasing interlocking mechanism of the present invention provides the additional safety feature of preventing the collet from opening during operation, which prevents the saw blade from being accidently releasing during use of the medical device.

Figure 1:
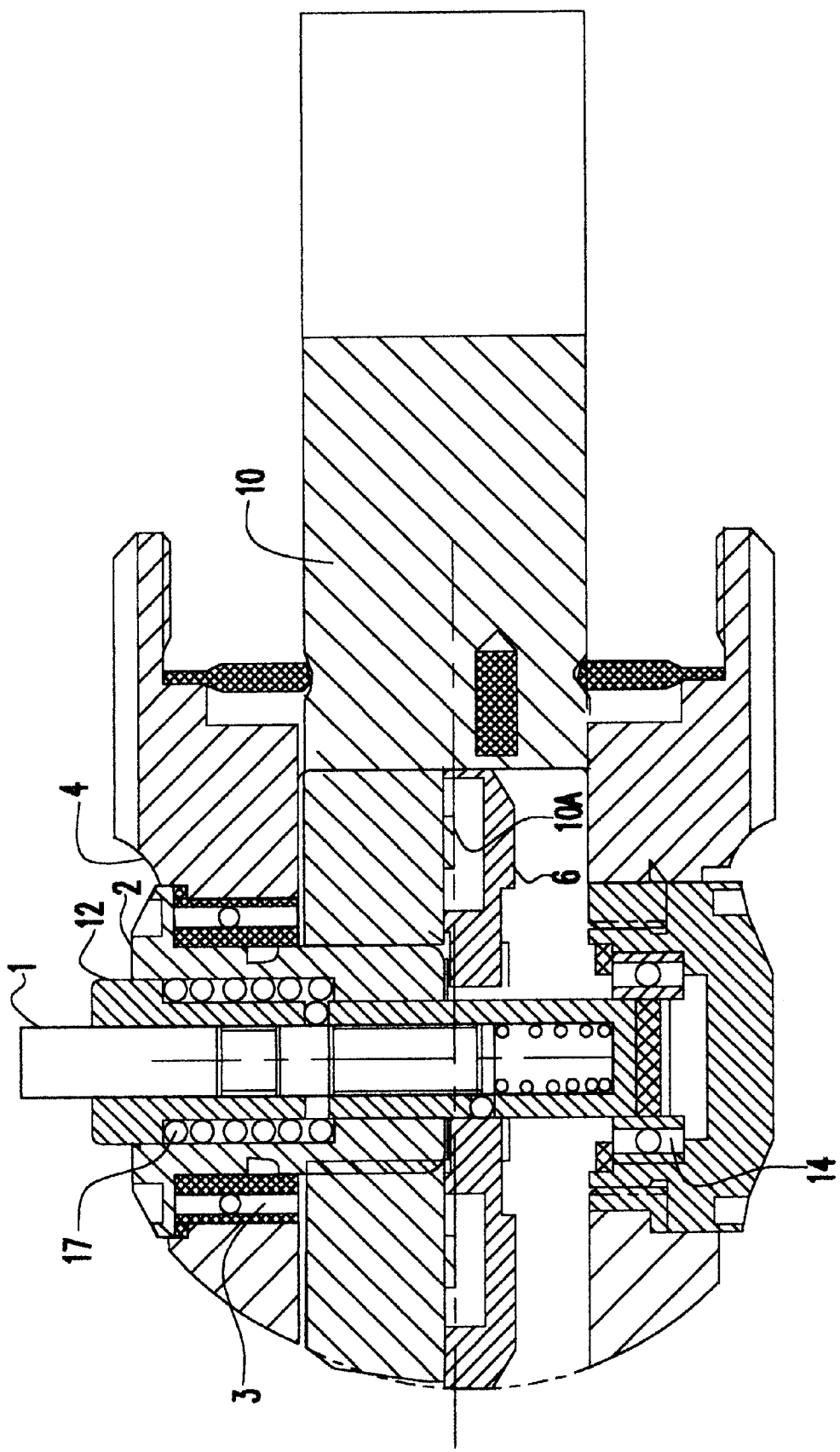
FIG. 1 is a side sectional view of the interlocking system of the present invention.

Referring now to FIG. 1, a side sectional view of the interlocking system of the present invention is shown. In particular, a release rod 1 is positioned within a release button 12. In turn, the release button 12 is positioned within a release cap 2 such that the release rod 1, release button 12 and release cap 2 are freely rotatably with respect to a stationary jaw head 4. In order to accomplish this, an upper bearing assembly 3 is used to mount the release cap 2 to the jaw head 4, and a lower bearing assembly 14 further communicates with a lower portion of the release button 12 at a lower portion of the jaw head 4.

A yoke 10 is positioned within the jaw head 4 at a substantial perpendicular orientation with respect to the release rod 1 and the release button 12. In a preferred embodiment, the yoke 10 is in threadable communication with the release cap 2 such that the yoke 10 is also freely rotatably with respect to the jaw head 4. However, it is not critical to the understanding of the present invention for the yoke 10 to be in threadable communication with the release cap 2 or freely rotatably with respect to the jaw head 4.

The yoke 10 includes downward extending projections 10a which hold the hub of the sagittal saw blade when the saw blade is inserted within collet of the present invention. A lock dish 6 is slidably mounted on the yoke 10, and in a closed position preferably communicates with a portion of the hub of the saw blade in order to prevent the saw blade from being released from the interlocking system of the present invention. In this closed position, the extending projections 10a of the yoke 10 extend through apertures of the hub of the saw blade and the lock dish 6 locks the hub of the saw blade into the collet (e.g., yoke 10 and lock dish 6). In embodiments, the hub of the saw blade may instead include extensions that extend into apertures of the yolk.

The lock disk 6 opened and closed by the action of the release button 12 such that when the release button 12 is depressed by the user, the lock dish 6 disengages from the lock dish 6 from the yoke 10 so that the hub of the saw blade can be inserted (or removed) into the collet. Once the hub of the saw blade is inserted into the collet, a spring 17 urges the release button 12 into an extended (e.g., upright) position which, in turn, urges the lock dish 6 against the hub of the saw blade and the extending projections 10a of the yoke 10 through the apertures of the hub of the saw blade. This mechanism locks the saw blade in the collet until both the release button 12 and release rod 1 are again fully depressed.

In order for the release button 12 to control the lock dish 6, the release button 12 extends through an aperture of the yoke 10 and is fixed to the lock dish 6 by, preferably, snap rings 16. However, other attachment mechanisms for attaching the release button 12 to the lock dish 6, such as, for example, locking pins, are also contemplated for use by the present invention. The lock dish 6 is also freely rotatably with respect to the stationary jaw head 4, and the release button 12 communicates with the lower bearing assembly 14 in order to provide further stability to the locking system of the present invention.

Figure 2:
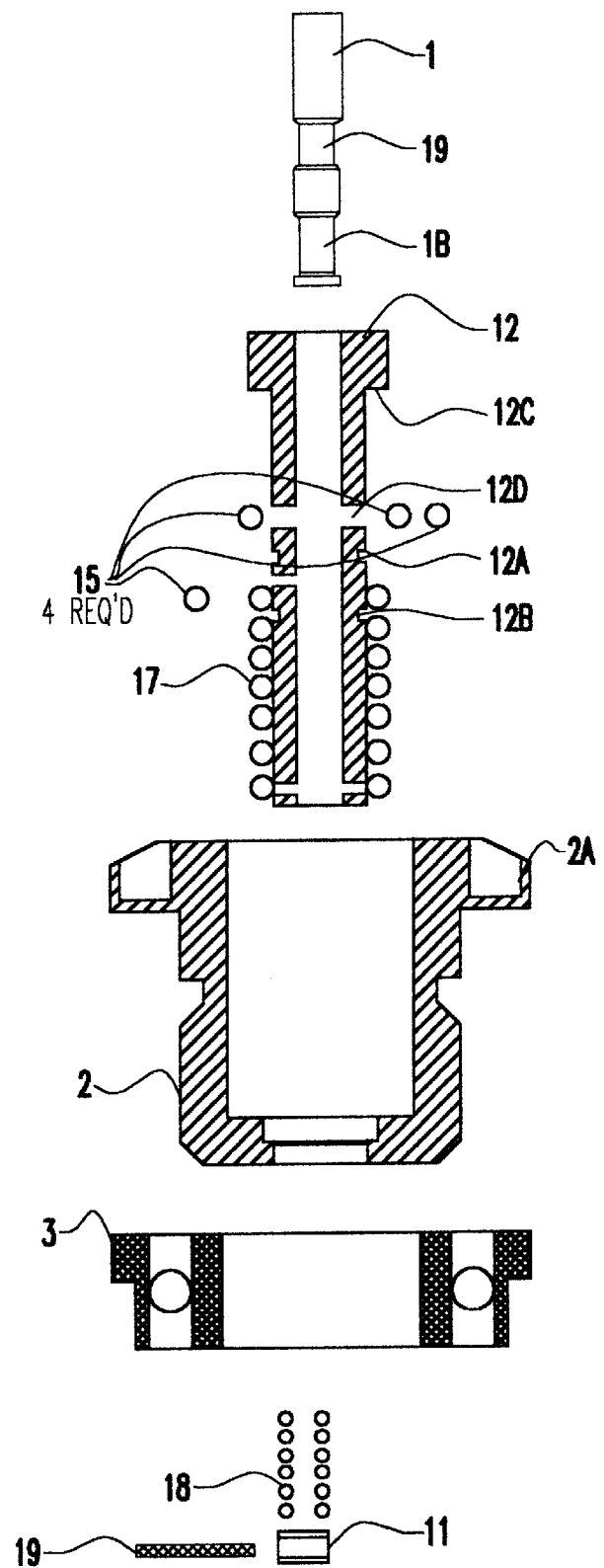
FIG. 2 is an exploded view of an upper assembly portion of the interlocking system of the present invention.

FIG. 2 shows an exploded view of an upper assembly portion of the interlocking system of the present invention. Specifically, FIG. 2 shows the release rod 1 having a top circumferential groove 1a and a bottom circumferential groove 1b. The release rod 1 is provided within a bore of a release button 12 and a spring cap 11 is inserted into the bore at a bottom of the release button 12 and is held in place by a pin 19. A spring 18 is positioned within the bore and positioned between the spring cap 11 and a bottom portion of the release rod 1. The spring 18, similar to the spring 17, urges the release rod 1 to a fulled extended (e.g., upright) position.

Referring further to FIG. 2, the release button 12 includes an upper circumferential groove 12a and lower circumferential groove 12b, and apertures 12d for the placement of locking balls 15. The upper and lower circumferential grooves 12a, 12b communicate with the snap rings 16 in order to fix the lock dish 6 to the release button 12 when the interlocking system is completely assembled. The locking balls 15 prevent the release button 12 from being depressed prior to the release rod 1 being depressed. This mechanism prevents the lock dish 6 from opening during use of the medical device, thus ensuring that the saw blade will remain within the collet. However, when the release rod 1 is depressed, and preferably flush with the upper portion of the release button 12, the locking balls 15 fall into the top circumferential groove 1a of the release rod 1 which allows the release button 12 to be depressed. This, in turn, permits the locking dish 6 to be opened so that the saw blade can be inserted (or removed) from the collet.

The release button 12 also includes an upper flange portion 12c having a diameter larger than the outer diameter of the remaining lower portion of the release button 12. The outer diameter of the lower portion of the release button 12 is slidably inserted within the release cap 2. In a preferred embodiment, the release cap 2 includes the lower inward facing flange 2a so that a spring 17 can be positioned between the upper flange portion 12c of the release button 12 and inward facing flange 2a of the release cap 2. The stiffness of the spring 17 is greater than the stiffness of the spring 18 which permits the release rod 1 to be depressed without the release button 12 being simultaneously depressed.

The bearing assembly 3 is placed proximate to the outer diameter of the release cap 2 and is further positioned underneath an upper outward facing flange 2b of the release cap 2. The bearing assembly 3 allows the release button 12 and release rod 1 assembly, including the yoke 10 and the lock dish 6, to be freely rotatable with respect to the stationary jaw head 4.

Figure 3:
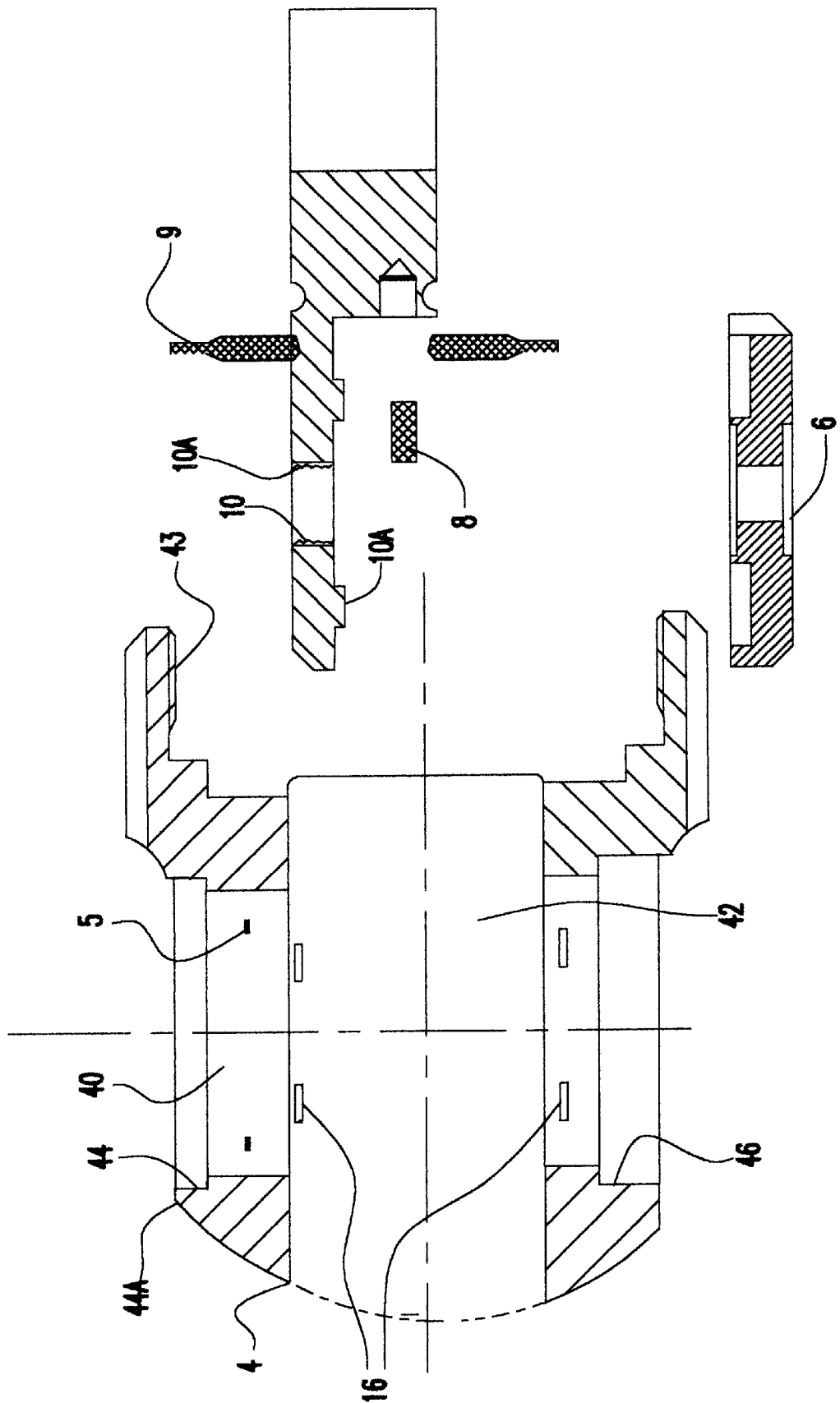
FIG. 3 is an exploded view of a mid-assembly portion of the interlocking system of the present invention.

FIG. 3 shows an exploded view of a mid-assembly portion of the interlocking system of the present invention. That is, FIG. 3 shows a detailed view of the collet system which includes the yoke 10 and the locking dish 6. The jaw head 4 may be any known jaw head and is not critical to the understanding of the present invention. However, for illustrative purposes only, one embodiment of the jaw head 4 will be described herein. It is well understood, however, that the following description of the jaw head 4 is but only one embodiment, and other embodiments are equally contemplated for use with the present invention.

For illustrative purposes only, one example of the jaw head 4 includes a bore 40 for accommodating the upper assembly, as discussed with reference to FIG. 2 and seen clearly in FIG. 1. This bore 40 includes an upper shelf 44 and a lower shelf 46. In preferred embodiments, a flange of the bearing assembly 3 sits on the upper shelf 44 of the jaw head 4 and the flange of the release cap 2 sits proximate to the outer upper surface 44a of the jaw head 4. The jaw head 4 also includes a slot 42 to accommodate the yoke 10 and lock dish 6. As clearly seen in FIG. 1, when the yoke 10 and lock dish 6 are fully assembled, they fit within the slot 42 such that the yoke 10 and lock dish 6 are freely rotatable with respect to the jaw head 4.

The yoke 10 includes a threaded aperture 10a which communicates with a threaded portion of the release cap 2. This enables the release cap 2 (and the release button 12 and the release rod 1) to rotate at the same orientation as the yoke 10 with respect to the jaw head 4. Seals 9 are further provided between the yoke 10 and extensions 43 of the jaw head 4. The seals 9 are not critical to the understanding of the present invention, and are merely provided to ensure that there is a proper seal between the yoke 10 and the jaw head 4. A pin 8 is also provided within an aperture of the yoke 10 and keys to the lock dish 6 in order to prevent the lock dish 6 from rotating with respect to the yoke 10. The snap rings 16 are placed within the upper and lower circumferential grooves 12a, 12b of the release button 12, and are further positioned proximate to an upper and lower surface of the locking dish 6 in order to fix the lock dish 6 to the release button 12.

Figure 4:
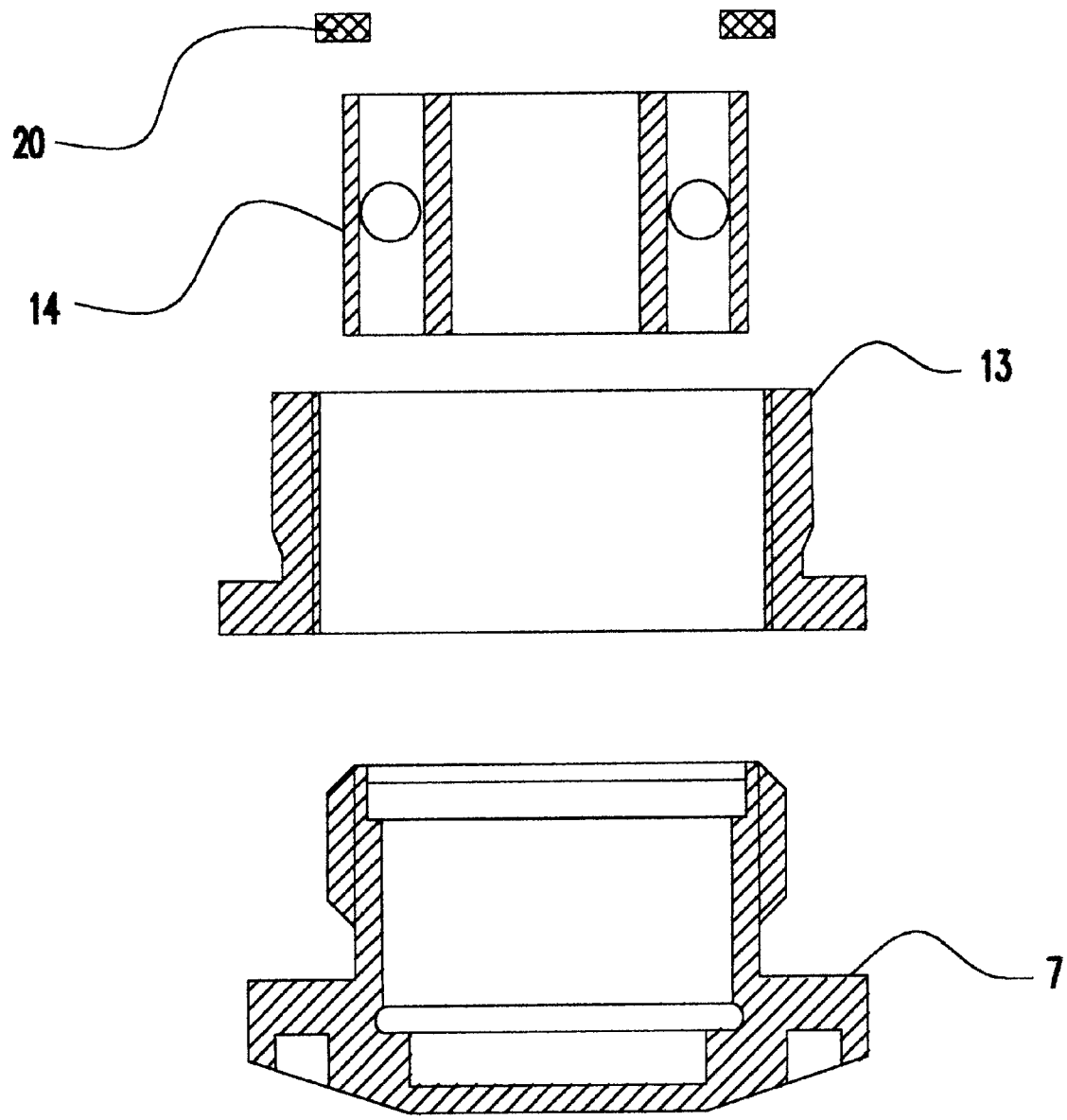
FIG. 4 is an exploded view of a lower assembly portion of the interlocking system of the present invention.

FIG. 4 is an exploded view of a lower assembly portion of the interlocking system of the present invention. The lower assembly includes an insert 13 which rests on the lower shelf 46 of the jaw head 4. In preferred embodiments, the lower bearing assembly 14 fits within the insert 13 and a bottom cap 7 closes the entire bottom portion so that the release button 12 cannot extend past the bottom cap 7. A snap ring 20 fixes the lower bearing assembly 14 to the insert 13, and the lower bearing assembly 14 further provides support for the release button 12 when in both the depressed and upright position.

In preferred embodiments, the release button 12 extends through the bore 40 of the jaw head 4, the threaded aperture 10a of the yoke and an aperture of the locking dish 6 in order to communicate with the lower bearing assembly 14.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A two stage releasing interlocking system for mounting a medical device tool, comprising;

a jaw head having an aperture;

a collet having an upper portion and a lower portion, the upper portion having an aperture, the aperture of the jaw head and the aperture of the upper portion being aligned;

moving means for moving the lower portion of the collet into an opened and a closed position with respect to the upper portion of the collet, the moving means extending through the apertures of the jaw head and the collet; and actuating means for locking both the moving means a the lower portion of the collet in the closed position when the actuating means is in a first position, wherein the moving means is unlocked and is capable of moving the lower portion of the collet into the opened position when the actuating means is in a second position.

2. The two stage releasing interlocking system of claim 1, wherein the moving means comprises a release button having an upper circumferential groove and a lower circumferential groove.

3. The two stage releasing interlocking system of claim 2, further comprising snap rings communicating with the upper and lower circumferential grooves of the release button, the lower portion of the collet being fixed to an outer portion of the release button between the snap rings.

4. The two stage releasing interlocking system of claim 1, wherein the upper portion of the collet is a yoke having extending portions that extend through apertures of a tool.

5. The two stage releasing interlocking system of claim 4, further comprising a retaining cap threadably contacting the upper portion of the yoke and housing the moving means and a portion of the actuating means, the retaining cap, the yoke and the moving means being rotatable with respect to the jaw head.

6. A two stage releasing interlocking system for mounting a medical device tool, comprising:

a jaw head having an aperture;

a collet having an upper portion and a lower portion, the upper portion having an aperture, the aperture of the jaw head and the aperture of the upper portion are aligned;

moving means for moving the lower portion of the collet into an opened and a closed position with respect to the upper portion of the collet, the moving means extending through the apertures of the jaw head and the collet;

actuating means for preventing the moving means from moving the lower portion of the collet into the opened position when the actuating means is in a first position and for permitting the moving means to move the lower portion of the collet in the opened position when the actuating means is in a second position, wherein the actuating means comprises:

a release cap inserted into the apertures of the jaw head and the upper portion of the collet, the release cap having a collar;

a release button slidably in contact with a bore of the release cap, the release button has at least one aperture and an outer diameter substantially equal to an inner diameter of the collar;

at least one locking bearing positioned within the at least one aperture of the release button and which extends from the outer diameter of the release button when the release button is in the first position thereby preventing the release button from sliding within the collar; and a release rod slidably in contact with a bore of the release button, the release rod has an upper circumferential groove, when the release rod is in a depressed position, the at least one locking bearing falls into the upper circumferential groove thereby permitting the release button to slide downward within the collar thus permitting the lower portion of the collar to be in the opened position when the release button slides downward in the collar.

7. The two stage releasing interlocking system of claim 6, wherein the release button and the collet is locked in place when the release rod is in the first position.

8. The two stage releasing interlocking system of claim 6, further comprising a spring positioned between a flange on the release button and the collar of the release cap, the spring urging the release button into the first position.

9. The two stage releasing interlocking system of claim 6, further comprising a spring placed in the bore of the release button and contacting a bottom surface of the release rod, the spring urging the release rod into an upright position such that the at least one locking bearing disengages from the upper circumferential groove thus locking the lower portion of the collet in the closed position.

10. The two stage releasing interlocking system of claim 1, further comprising a bearing assembly contacting the moving means such that the moving means and the collet are rotatable with respect to the jaw head.

11. The two stage releasing interlocking system of claim 10, wherein the bearing assembly includes an upper bearing and a lower bearing.

12. The two stage releasing interlocking system of claim 10, wherein the lower portion of the collet is fixed to the upper portion of the collet via a spring mechanism that the lower portion and the upper portion are rotatably fixed with respect to one another.

13. A two stage releasing interlocking system for mounting a medical device tool, comprising;
   a jaw head having an aperture;
   a collet having an upper portion and a lower portion, the upper portion having an aperture, the aperture of the jaw head and the aperture of the upper portion being substantially aligned;
   moving means for moving the lower portion of the collet into an opened and a closed position with respect to the upper portion of the collet, the moving means extending through the apertures of the jaw head and the collet;
   a release rod slidable within a bore of the moving means; and
   actuating means for locking the moving means and the lower portion of the collet in the closed position when the release rod is in a first position,
   wherein the moving means is unlocked and is capable of moving the lower portion of the collet into the opened position when the release rod is in a second position.

14. The two stage releasing interlocking system of claim 13, wherein the moving means is a release button which has upper and lower circumferential grooves that contact upper and lower snap rings, the upper and lower snap rings hold the lower portion of the collet to the release button.

15. The two stage releasing interlocking system of claim 13, further comprising:
   a retaining cap threadably contacting the upper portion of the collet; and
   a bearing assembly being positioned within the jaw head and housing the retaining cap, the retaining cap and upper and lower portions of the collet being rotatable with respect to the jaw head.

16. A two stage releasing interlocking system for mounting a medical device tool, comprising:
   a jaw head having an aperture;
   a collet having an upper portion and a lower portion, the upper portion having an aperture, the aperture of the jaw head and the aperture of the upper portion are substantially aligned;
   moving means for moving the lower portion of the collet into an opened and a closed position with respect to the upper portion of the collet, the moving means extending through the apertures of the jaw head and the collet;
   a release rod slidable within a bore of the moving means;
   actuating means for preventing the moving means from moving the lower portion of the collet into the opened position when the release rod is in a first position and for permitting the moving means to move the lower portion of the collet in the opened position when the release rod is in a second position, wherein the actuating means comprises
      a release cap inserted into the apertures of the jaw head and the upper portion of the collet;
      a release button slidably in contact with a bore of the release cap, the release button has at least one aperture and an outer diameter substantially equal to a diameter of the collar;
      at least one locking bearing positioned within the at least one aperture of the release button, the at least one locking bearing extends from the outer diameter of the release button when the release button is in a first position,
      wherein the release rod is slidably in contact with a bore of the release button and has an upper circumferential groove which locks the at least one locking bearing when the release rod is in a locked closed position.

17. The two stage releasing interlocking system of claim 16, further comprising:
   a first spring being placed in the bore of the release button and contacting a bottom surface of the release rod, the first spring urging the release rod into the first position so that the at least one locking bearing disengages from the upper circumferential groove and locks the release button into the first position; and
   a second spring being positioned between a flange on the release button and a collar of the release cap, the spring urging the release button into the first position.

18. A two stage releasing interlocking system for mounting a medical device tool, comprising:
   a jaw head having an aperture;
   a collet having an upper portion and a lower portion, the upper portion having an aperture and being mounted to the collet such that the aperture of the jaw head and the aperture of the upper portion are substantially aligned;
   a release button having circumferential grooves which contact snap rings, the snap rings hold the lower portion of the collet to an outer portion of the release button, the release button further moving the lower portion of the collet into an opened and a closed position with respect to the upper portion of the collet;
   a release rod slidable within a bore of the release button; and
   actuating means for locking the release button such that the lower portion of the collet is locked in the closed position when the release rod is in a first position;
   wherein the moving means and the release button are unlocked and capable of moving the lower portion of the collet into the opened position when the release rod is in a second position.

* * * * *